United States Patent
Haindl et al.

(10) Patent No.: US 8,298,212 B2
(45) Date of Patent: Oct. 30, 2012

(54) PORT SYSTEM WITH OPPOSING CLAMPING JAWS

(75) Inventors: Hans Haindl, Wennigsen (DE); Christoph Jochum, Nidderau (DE); Frank M. Roediger, Bissendorf (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 10/574,427

(22) PCT Filed: Sep. 3, 2004

(86) PCT No.: PCT/EP2004/009834
§ 371 (c)(1),
(2), (4) Date: Apr. 3, 2006

(87) PCT Pub. No.: WO2005/032645
PCT Pub. Date: Apr. 14, 2005

(65) Prior Publication Data
US 2007/0123831 A1    May 31, 2007

(30) Foreign Application Priority Data
Oct. 2, 2003    (DE) .................................. 103 46 470

(51) Int. Cl.
*A61M 39/02* (2006.01)
*A61M 25/18* (2006.01)
*A61M 37/00* (2006.01)

(52) U.S. Cl. ................................... 604/539; 604/288.01

(58) Field of Classification Search ............ 604/288.01–288.04, 533–535, 604/539
See application file for complete search history.

(56) References Cited

U.S. PATENT DOCUMENTS

| | | | |
|---|---|---|---|
| 4,464,178 A | 8/1984 | Dalton et al. | |
| 4,723,948 A | 2/1988 | Clark et al. | |
| 4,772,270 A | 9/1988 | Wiita et al. | |
| 5,167,638 A * | 12/1992 | Felix et al. | 604/175 |
| 5,232,453 A * | 8/1993 | Plass et al. | 604/180 |
| 5,607,393 A | 3/1997 | Ensminger et al. | |
| 5,718,682 A * | 2/1998 | Tucker | 604/288.02 |
| 6,165,157 A * | 12/2000 | Dillon et al. | 604/263 |
| 6,213,973 B1 | 4/2001 | Eliasen et al. | |

FOREIGN PATENT DOCUMENTS
DE    41 29 781    3/1993
* cited by examiner

*Primary Examiner* — Kevin C. Sirmons
*Assistant Examiner* — Bradley Osinski
(74) *Attorney, Agent, or Firm* — Occhiuti Rohlicek & Tsao LLP

(57) ABSTRACT

The invention relates an implantable access device for a catheter for supplying an active substance to an active site. The inventive access device comprises a chamber which is arranged in a housing for receiving the active substance and is closed with a piercable membrane. A connecting piece, to which the catheter is connectable, is fluidly connected to the chamber. The catheter is fixed by clamps that are fixable to the housing preferably by means of elastic fixing arms. The chamber receiving the active substance is embodied in an insertion element that is arranged in a recess of the housing by an intermediate clamping of the intermediate layer of the membrane in such a way that the insertion element produces a pressure force to said membrane.

20 Claims, 5 Drawing Sheets

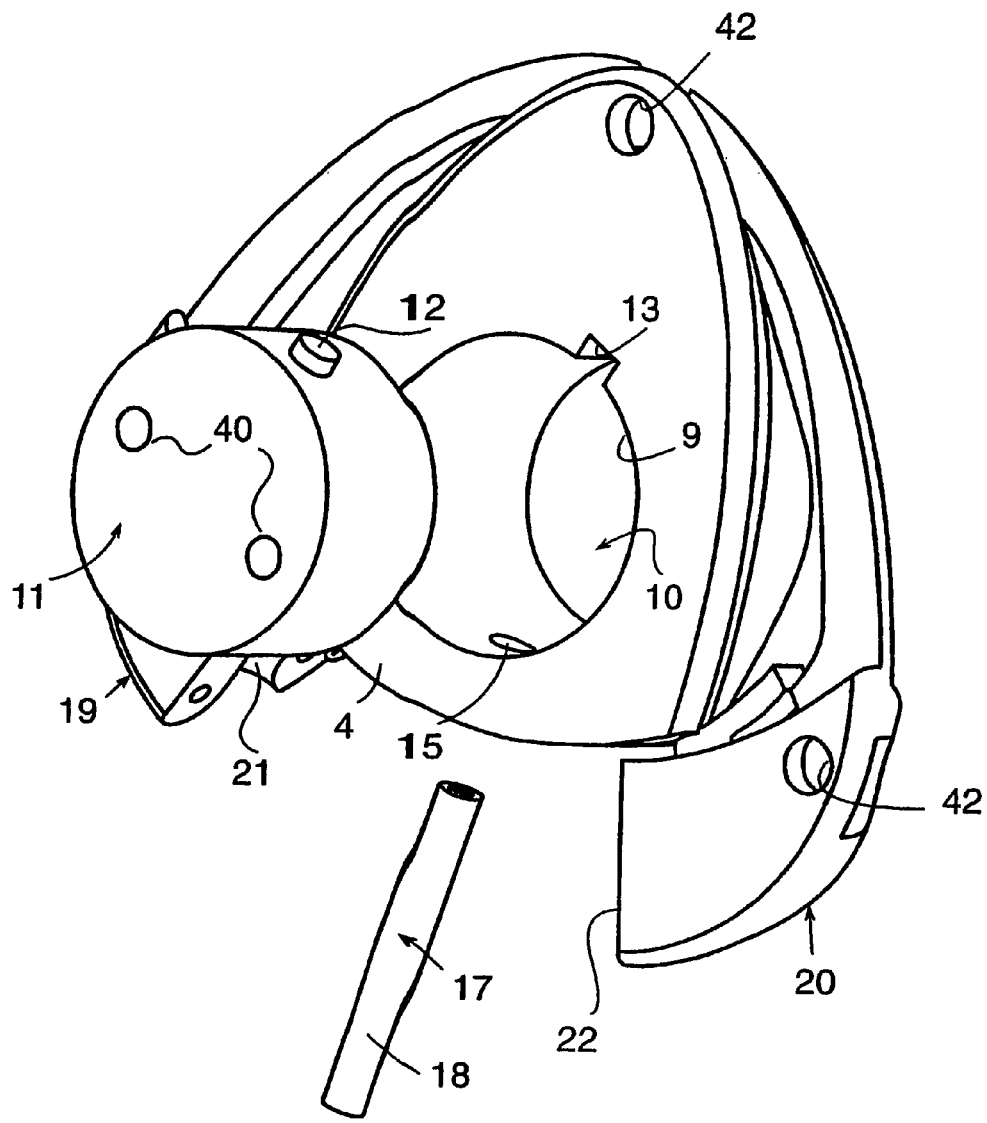
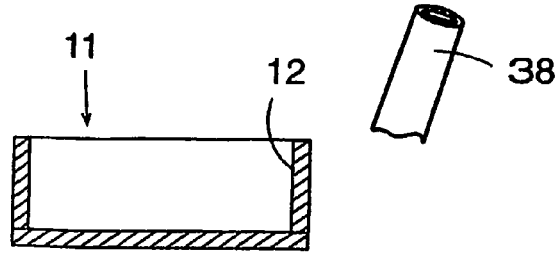
Fig. 3
Fig. 6

PORT SYSTEM WITH OPPOSING CLAMPING JAWS

PRIORITY APPLICATIONS

This application is a 371 of PCT/EP04/09834, filed Sep. 3, 2004. This application also claim priority to German application 103 46 470.0, filed Oct. 2, 2003.

FIELD OF INVENTION

The invention relates to a port system which is implanted to provide access to a remotely situated site of action to which an active substance is to make its way. The port system has a subcutaneously implantable housing in which is arranged a chamber for receiving the active substance. The chamber in the port is closed off by a piercable membrane which is situated below the skin. For injection of the active substance, the skin and the membrane are pierced by a needle and the active substance is injected into the chamber. From the chamber, the active substance then makes its way to the site of action via a catheter.

BACKGROUND OF THE INVENTION

The present invention offers many advantages over previous port systems. DE 41 29 782 C1 describes a port system that comprises a port and a catheter. The port has a housing with an opening at the bottom to receive the active substance and an opening at the top to receive the membrane. The membrane is held in the opening by a clamping ring which exerts a pressure on the membrane so that the membrane curves outwards. The use of a clamping ring is disadvantageous because it makes it difficult to secure the membrane over the opening. For example, in an adhesive-bonded or welded connection, it is necessary for the clamping ring, which is under pressure, to be held in position against the housing until the adhesive has cured.

For the connection of the catheter, the known port has a tapering connecting piece that is in fluid connection with the central opening in the housing. The catheter is pushed onto the tapering connecting piece. The catheter is fixed to the connecting piece by means of a clamping sleeve which is screwed to the housing. A coupling of this kind for flexible lines is described in detail in DE 41 29 781 A 1. It is a disadvantage that, once the clamping sleeve has been fitted, it cannot be seen how far the catheter has been pushed onto the tapering connecting piece. Further, if not properly fitted, there is a risk the flexible catheter will come loose from the connecting piece. Still further, it is a disadvantage that the clamping sleeve is a separate component and can easily be lost.

When an active substance is injected with a needle, care must be taken to ensure that the membrane situated beneath the skin is accurately targeted. If the needle impacts the housing, instead of the membrane, there is a possibility the needle will slip off the housing and strike the catheter.

SUMMARY OF THE INVENTION

An object of the invention is to provide a port for a catheter that can be assembled simply and inexpensively. In accordance with this objective, the invention provides a port that allows the membrane to be easily fixed into place in the housing and the catheter to be easily fixed to the connecting piece.

A further object of the invention is to reduce the risk of the catheter being injured when an active substance is injected into the port.

In an embodiment of the invention, the port may have two clamping jaws, with clamping faces, for the fixing of the catheter to the connecting piece. The clamping jaws may be connected to the housing and situated opposite one another. The clamping jaws can be moved from a first position, in which they are spaced away from the housing laterally, to a second position in which they fix the catheter in place between their clamping faces by a clamping action. The clamping jaws, when they are spaced away from the housing laterally, have the advantage that they do not obstruct the view when the catheter is being pushed onto the connecting piece. Hence the seating of the catheter on the connecting piece can be checked. It is also advantageous that the doctor is not obstructed by the clamping jaws when pushing on the catheter. To fix the catheter to the connecting piece, the clamping jaws merely need to be moved to the second position. Handling is simplified in this way.

In an embodiment of the invention, the clamping jaws may be fastened to the housing by fastening arms having a resilient form. It is advantageous that the clamping jaws are securely fastened to the housing by the resilient fastening arms and are easy to move. It is also advantageous that the resilient fastening arms do not make it necessary for complicated fastening techniques to be employed. The clamping jaws may also be fastened to the housing by means of joints or sliders.

In an embodiment of the invention, the fastening arms may form a clasp which fits round the sides of the housing and which fasten to the housing at the opposite end from the connecting piece. This further simplifies the structure. The fastening arms in the form of a clasp may be produced as a separate item, e.g., through injection moulding, and may be connected to the housing at a later stage. It is, however, equally possible for the clasp to be produced together with housing. The fastening of the clasp to the end of the housing opposite the connecting piece makes it possible for the clamping jaws to have a relatively large range of movement. Consequently, the clamping jaws may be spaced a relatively long distance away from the housing laterally in the first position, thus creating a clear space which is as large as possible in the region of the connecting piece.

In an embodiment of the invention, provision may be made for the clamping jaws to be locked to the housing by latching in the second position. Because the clamping jaws have a secure grip on the housing, it is ensured that the connection will not come loose.

In an embodiment of the invention, the housing may have lateral guide grooves in which the clamping jaws are guided. This ensures that, although the clamping jaws are able to be spaced away laterally, they do nevertheless have a grip on the housing.

In an embodiment of the invention, the clamping jaws may be secured to the housing by latching. Steps may be formed in the guide grooves and the clamping jaws may have latching hooks. Additional fixing may be obtained by giving the clamping jaws spigots and holes which are associated with one another. When the clamping jaws are pressed together, the spigots engage in the holes, thus producing an engaged connection.

In an embodiment of the invention, assembly of the port may be further facilitated by virtue of the chamber being formed in an insert element, which may be locked in an opening in the housing with the membrane interposed and clamped such that the insert element exerts an applying pressure on the membrane. The insert element thus not only forms the chamber for the active substance but also represents an assembling part by which the membrane is fixed in place under pressure. Once the membrane has been fixed in place, both the insert element and the membrane may be welded or adhesive-bonded to the housing. It is advantageous that the membrane can be preloaded without any additional clamping device.

In an embodiment of the invention, the insert element and the housing may form a bayonet connection. The bayonet connection enables the insert element to be locked easily and securely in the housing. Other methods, such as screwing the insert element to the housing, may also be employed.

In an embodiment of the invention, the insert element may have a projecting step and the opening in the housing may have a groove with a lateral undercut in which the insert element seats.

In an embodiment of the invention, the insert element may be held securely in the housing by virtue of the fact that the connecting piece is a canula which is inserted in mutually aligning holes in the housing and the insert element. The canula thereby stops the insert element from twisting in the housing, and the projecting step is thus securely seated in the lateral undercut. It is also advantageous that the canula, insert element and housing are held in position with a slight clamping action when they are being adhesive-bonded.

In an embodiment of the invention, a seal may be obtained by pressing adhesive into the gap between the insert element, membrane and housing. The adhesive may be injected into the groove in the housing. To also simplify the bonding of the canula too, channels which start from the groove and run to the mutually aligning holes in the housing and the insert element may be provided in the wall of the insert element.

In an embodiment of the invention, the undercut and the mutually aligning holes in the housing and the insert element may be arranged diametrically opposite one another, thereby simplifying the removal of the work pieces from the mould at the time of manufacture.

In an embodiment of the invention, the risk of the catheter being injured by the injection needle may be avoided by providing a projecting step on the upper side of the port between the membrane and the connecting piece. If the injection needle impacts on the housing instead of the membrane, the projecting step stops the needle from slipping off the port and piercing the catheter.

In an embodiment of the invention, the projecting step is formed on the clamping jaws, which fit firmly around the catheter pushed onto the connecting piece. The clamping jaws thus serve not only to fix the catheter in place but also to protect it.

BRIEF DESCRIPTION OF THE DRAWINGS

FIG. 3 is an exploded view of the port from below, with the clamping jaws spaced away from the housing.

FIG. 6 is a cross sectional view of the insert element.

DETAILED DESCRIPTION

In the following, embodiment examples of the apparatus in accordance with the invention are explained in more detail by reference to the drawings.

Figure 1:
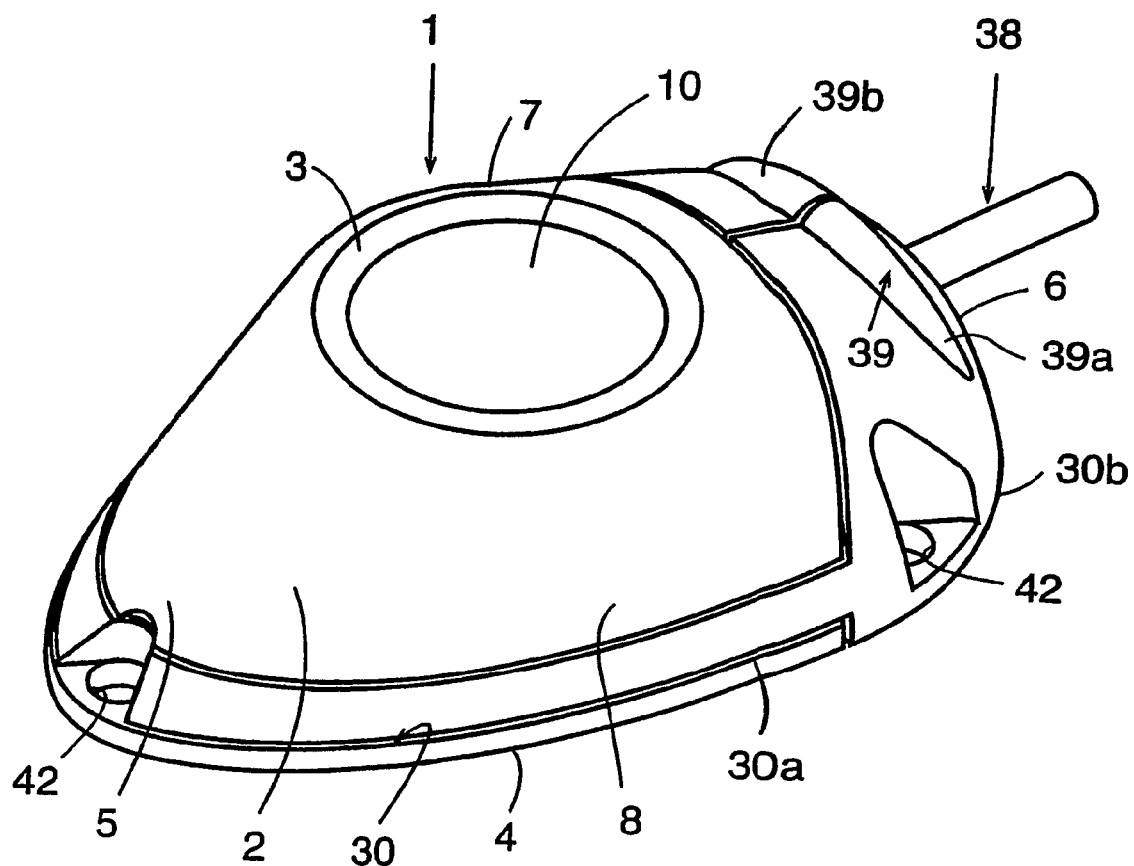
FIG. 1 is a view of the port from above, showing the clamping jaws resting against the housing.

FIG. 1 is an enlarged view from above of the port-catheter, which comprises a port 1 and a catheter 38. The port 1, which may be approximately the size of a fingertip and has a shallow housing 2 that is implanted subcutaneously. The upper side, which lies under the skin of the housing 2, is identified by reference numeral 3, its underside by reference numeral 4, its front end by reference numeral 5, its rear end by reference numeral 6 and its longitudinal sides by reference numerals 7 and 8. The longitudinal sides 7 and 8, of the housing 2, run to the front end 5 of the housing at a shallow angle. The housing 2 is thus shaped like a computer mouse.

The housing 2 may, for example, be produced from plastics material by injection moulding. It may also be composed of other compatible materials such as metals or ceramics. Housing 2 has a central cylindrical opening 9 (FIG. 3) which is closed off by a circular piercable membrane (septum) 10. The membrane 10, which is inserted in the opening 9 and which is of a diameter that approximately corresponds to opening 9, is supported against an abutment (not shown) which extends around at the top end of the opening 9. The upper side of the membrane 10 is exposed at the upper side of the housing 2, thereby enabling it to be pierced by an injection needle.

Figure 2:
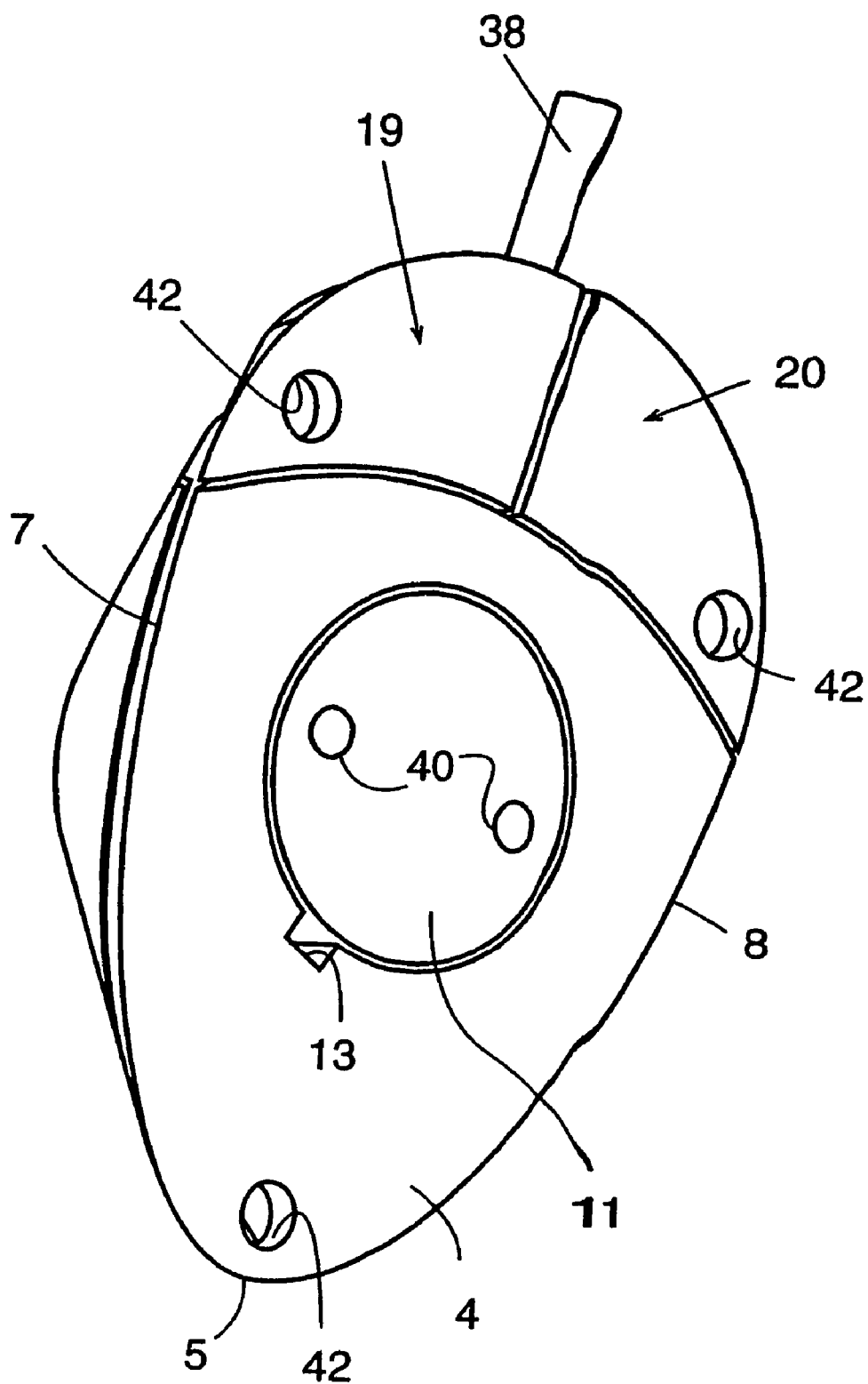
FIG. 2 is a view of the port from below, showing the clamping jaws resting against the housing.

A cylindrical insert element 11 is inserted in the central opening 9 in the housing 2 as a good fit (FIG. 2), i.e., a secure tight fit. A cylindrical chamber 12a is formed in the insert element 11 to receive the active substance to be administered (FIG. 6).

It is an advantage that the insert element 11 can be produced, independently of the housing 2, from different compatible materials, such as plastics or metals, without the entire port having to be altered. For example, insert element 11 may be made from titanium or ceramic material. This is an important consideration particularly when the insert element comes into contact with blood taken in via the catheter because different materials have different levels of acceptability with regard to compatibility with blood.

Figure 4:
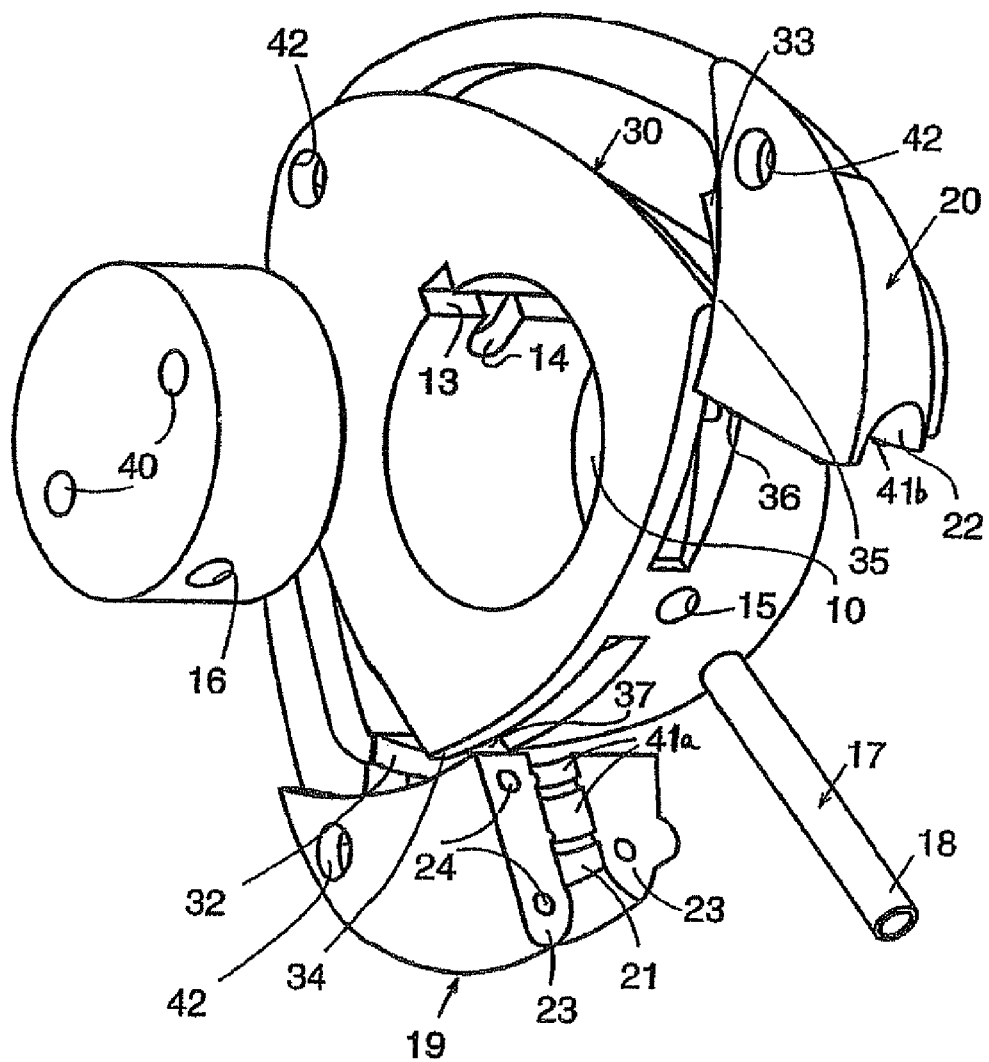
FIG. 4 is a second exploded view of the port from below, from a different direction than FIG. 3, with the clamping jaws spaced away from the housing.

The insert element 11 forms, with the housing 2, a bayonet connection. For this purpose, the insert element 11 has a projecting cylindrical step 12 and the opening 9 has a axial groove 13 in its wall into which the step 13 can be pushed as a good fit. To lock the step 12, the groove 13 has a lateral undercut 13 in which the step 12 engages when the insert element 11 is twisted (FIG. 4). The bayonet connection is designed so that the insert element 11 exerts an adequate applying pressure on the membrane 10 for the membrane 10 to curve outwards.

At the rear end 6, the housing 2 has a hole 15, which aligns with a hole 16 of the same diameter in the cylindrical wall of the insert element 11 when the insert element 11 has been inserted in the housing 2 and locked by twisting. The holes 15 and 16 in the housing 2 and in the insert element 11 are situated diametrically opposite the undercut 14, the groove 13 being offset sideways for this purpose. Advantages for production arise from this arrangement at the time of removal from the mould.

Mounted in the mutually aligning holes 15 and 16, in the insert element 11 and the housing 2, is a tubular canula 17 whose projecting end portion forms the connecting piece 18 of the port 1 onto which the end portion of the catheter 38 is pushed. The end of the connecting piece 18 preferably tapers on the outside. The canula 17 which extends through the two holes 15 and 16 not only creates a fluid connection between the chamber 12a and the connecting piece 18 but also acts to secure the insert element 11 against twisting.

For assembly, the insert element 11 is inserted and locked in the opening 9 in the housing 2. This can be done with a suitable tool which has projections that engage in holes 40 in the insert element 11. The canula 17 is then pushed into the holes 15 and 16. Adhesive is then pressed into the groove 13 and distributes itself evenly via circular channels (not shown) which are provided in the wall of the opening 9 in the housing 2, thus causing the adhesive to completely fill the gap between the insert element 11, membrane 10, canula 17 and housing 2. The insert element 11, the membrane 10 and the canula 17 are thus sealed to the housing 2. Additional clamping devices and the like are not required during the curing of the adhesive because the insert element 11 inserted in the opening 9 is fixed in place by means of the bayonet connection and the canula 17.

Figure 5:
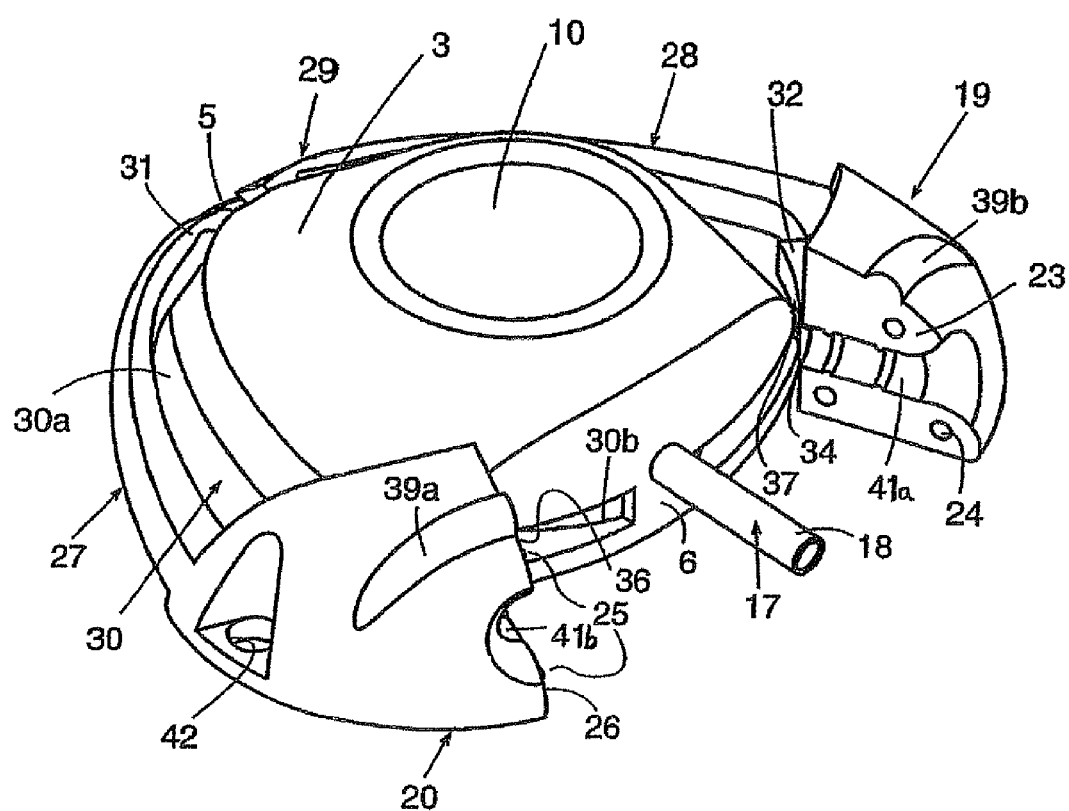
FIG. 5 is a view of the port from above, with the clamping jaws spaced away from the housing.

Catheter 38, which is pushed onto the connecting piece 18, is fixed in place on port 1 by two clamping jaws 19 and 20. The two clamping jaws 19 and 20 have respective clamping faces 21 and 22 corresponding to the diameter of the canula 17. The two clamping jaws 19 and 20 are movable between a first position (shown in FIGS. 3 to 5) and a second position (shown in FIGS. 1 and 2). In the second position, the clamping jaws 19 and 20 fit firmly around the catheter 38 so that the catheter 38 is securely mounted on the connecting piece 18. In the first position, on the other hand, the clamping jaws 19 and 20 are spaced away from the housing laterally so that there is enough free space for the catheter 38 to be pushed onto the connecting piece 18 and a visual check can be made of the catheter 38 when it is pushed onto the connecting piece 18.

The clamping jaws 19 and 20 are fastened to the housing 2 by respective fastening arms 27 and 28, which are of a resilient form. The fastening arms 27 and 28 form a U-shaped clasp 29, which is seated in guide grooves 30 extending at the front end 5 and along the longitudinal sides 7 and 8 of the housing 2. By its arcuate central portion 31, the clasp 29 is fastened to the front end 5 of the housing 2, thus allowing the lateral portions of the clasp 29 to splay outwards.

On their insides, the clamping jaws 19 and 20 have respective latching hooks 32 and 33 that slide in the guide grooves 30 when the fastening arms 27 and 28 splay apart. The guide grooves 30 are each in two parts. One part 30*a* extends along the longitudinal sides 7 and 8 of the housing 2 and the other part 30*b* extends along the rear end 6 of the housing 2. In the region of the transition between the two parts 30*a* and 30*b*, the guide grooves 30 form projecting steps 34 and 35. In the first position, in which the clamping jaws 19 and 20 are spaced away laterally, the inner faces of the latching hooks 32 and 33 are supported against the steps 34 and 35.

In the parts 30*b* of the guide grooves 30 at the rear end 6 of the housing 2, there are formed respective steps 36 and 37 against which the latching hooks 32 and 33 are supported when the clamping jaws 19 and 20 are in the second position in which they fix the catheter 38 in place by clamping. Provided in the end face 23 of one clamping jaw 19 are holes 24, in which spigots 25, which are provided on the end face 26 of the other clamping jaw 20, engage. Clamping ridges 41*a* and 41*b* are also provided on the clamping faces 21 and 22.

The outline of the clasp 30 and the outline of the clamping jaws 19 and 20, having the latching hooks 32 and 33 match the outline of the guide grooves 30 and the outline of the housing 2. This results in the clasp 30 and the clamping jaws 19 and 20 and the housing 2 fitting together securely. Provided in the front end 5 of the housing 2 and in the clamping jaws 19 and 20 are fixing holes 42 for a fabric. This allows the port 1 to be sewn onto a physical location.

Provided on the upper side of the clamping jaws 19 and 20 between the membrane 10 and the connecting piece 18 is a projecting step 39 that stops an injection needle, which impacts on the housing 2, from slipping off the housing 2 and injuring the catheter 38. The projection step 39 is in two parts 39*a* and 39*b*, each of which extends across the upper side of the relevant clamping jaw 19 and 20 substantially perpendicularly to the longitudinal axis of the connecting piece 18.

If the injection needle impacts on the upper sided of the housing 2 of the port 1 between the membrane 10 and the connecting piece 18, the needle might slip off in the direction of the connecting piece 18 and perforate the flexible catheter tube. This would make it necessary for the port 1 to be replaced, which is a surgically complicated. If the perforation is not detected, there is also a risk of the active substance not making its way to the site of action or not doing so in sufficient quantity. The active substance may also emerge at the wrong site of action, i.e. at the perforation. The projecting step 39 is able to prevent this because the injection needle impacts on the housing 2 with a certain amount of force, and if it slips off in the direction of the connecting piece 18 it will be diverted sideways by the step 39 substantially perpendicularly to the connecting piece 18.

The invention claimed is:

1. A port for a catheter, the port comprising:
   a chamber for receiving active substances, the chamber arranged in a housing and closed off by a piercable membrane,
   a connecting piece, the connecting piece capable of connecting to the catheter and in fluid communication with the chamber;
   movable clamping jaws, the clamping jaws having clamping faces that are situated opposite one another, the clamping jaws being movable from a first position, in which the clamping jaws are spaced away from the housing laterally, to a second position in which the clamping jaws fix the catheter in place between their clamping faces by a clamping action, the clamping jaws being connected to the housing when the clamping jaws are in each of the first position and the second position.

2. The port of claim 1, wherein the clamping jaws are fastened to the housing by fastening arms having a resilient form.

3. The port of claim 1, wherein the fastening arms form a clasp that fits around the sides of the housing and is fastened to the housing at the opposite end from the connecting piece.

4. The port of claim 1, wherein the clamping jaws are secured to the housing by latching in the second position.

5. The port of claim 1, wherein the housing has guide grooves that guide the clamping jaws.

6. The port of claim 5, wherein steps are formed in the guide grooves, and the clamping jaws have latching hooks which, in the second position, are locked to the steps by latching.

7. The port of claim 1, wherein the clamping jaws have spigots and holes that are associated with one another and engage in the second position.

8. The port of claim 1, wherein the chamber is formed in an insert element that is locked in an opening in the housing with the membrane interposed and clamped such that the insert element exerts an applying pressure on the membrane.

9. The port of claim 8, wherein the insert element and the housing form a bayonet connection.

10. The port of claim 8, wherein the insert element has a projecting step and the opening in the housing has a groove with a lateral undercut in which the projecting step on the insert element seats.

11. The port of claim 9, wherein the insert element has a projecting step and the opening in the housing has a groove with a lateral undercut in which the projecting step on the insert seats.

12. The port of claim 8, wherein mutually aligning holes are provided in the housing and the insert element, and the connecting piece is a cannula that is inserted in the holes in the housing and the insert element.

13. The port of claim 9, wherein mutually aligning holes are provided in the housing and the insert element, and the connecting piece is a cannula that is inserted in the holes in the housing and the insert element.

14. The port of claim 10, wherein mutually aligning holes are provided in the housing and the insert element, and the connecting piece is a cannula that is inserted in the holes in the housing and the insert element.

15. The port of claim 14, wherein the lateral undercut and mutually aligning holes are arranged diametrically opposite one another.

16. The port of claim 9, wherein at least one of the membrane and the insert element and the connecting piece are adhesive-bonded to the housing.

17. The port of claim 14, wherein at least one of the membrane and the insert element and the connecting piece are adhesive-bonded to the housing.

18. The port of claim 1, wherein the port is an injection moulding.

19. The port of claim 15, wherein the port is an injection moulding.

20. A port for a catheter, the port comprising:
- a chamber for receiving active substances, the chamber arranged in a housing and closed off by a piercable membrane,
- a connecting piece, the connecting piece capable of connecting to the catheter and in fluid communication with the chamber;
- movable clamping jaws, the clamping jaws having clamping faces that are situated opposite one another, the clamping jaws being movable from a first position, in which the clamping jaws are spaced away from the housing laterally, to a second position in which the clamping jaws fix the catheter in place between their clamping faces by a clamping action, the clamping jaws being connected to the housing when the clamping jaws are in each of the first position and the second position, and
- wherein the clamping jaws are movable relative to each other capable of clamping a catheter therebetween.

* * * * *